United States Patent [19]
Gerdt et al.

[11] Patent Number: 5,494,798
[45] Date of Patent: Feb. 27, 1996

[54] FIBER OPTIC EVANSCENT WAVE SENSOR FOR IMMUNOASSAY

[76] Inventors: David W. Gerdt; John C. Herr, both of P.O. Box 8175, Charlottesville, Va. 22906

[21] Appl. No.: 163,709

[22] Filed: Dec. 9, 1993

[51] Int. Cl.$^6$ .............................. C12Q 1/68; G01N 33/53
[52] U.S. Cl. .................................. 435/6; 435/7.1; 435/7.4; 435/7.8; 435/7.9; 436/501; 436/518; 436/527; 436/546; 422/82.06; 422/82.11; 385/13; 385/30; 356/448
[58] Field of Search .................................. 435/6, 7.1, 7.4, 435/7.8, 7.9; 436/501, 518, 527, 546, 164, 805, 807; 422/82.06, 82.11; 427/2, 2.11; 356/448; 385/13, 30

[56] References Cited

U.S. PATENT DOCUMENTS

| H1,212 | 7/1993 | Thames | 435/7.8 |
|---|---|---|---|
| 4,447,546 | 5/1984 | Hirschfeld | 436/527 |
| 4,634,858 | 1/1987 | Gerdt | 250/227 |
| 4,818,710 | 4/1989 | Sutherland et al. | 436/527 |
| 4,852,967 | 8/1989 | Cook et al. | 350/96.29 |
| 4,879,454 | 11/1989 | Gerdt | 219/494 |
| 4,909,990 | 3/1990 | Block et al. | 422/82.11 |
| 5,173,747 | 12/1992 | Boiarski et al. | 356/361 |
| 5,242,797 | 9/1993 | Hirschfeld | 435/6 |

OTHER PUBLICATIONS

Military Standard Glossary, Fiber Optics Dept of Defense United States of America MIL-STD-2196 (SH) 12 Jan. 1989 pp. 31, 42, 150, 153.
Vo–Dinh, T., et al., Fiber Optic Chemical Sensors and Biosensors, "Fiberoptics Immunosensors", vol. II, pp. 217–257, 1991.
Wolfbeis, Otto, Fiber Optic Chemical Sensors and Biosensors, vol. I, pp. 1–23, 1991.
Oxenford, Jeffrey L., "Development of a fiber optic chemical sensor for the monitoring of trichloroethylene in drinking water", SPIE vol. 1172 Chemical, Biochemical and Environmental Sensors pp. 108–114, 1989.
Kvasnik, Frank, et al., "Distributed chemical sensing utilising evanescent wave interactions", SPIE vol. 1172 Chemical, Biochemical, and Environmental Sensors, pp. 75–80, 1989.
Waldzak, Irene M., et al. "A sensitive Fiber Optic Immunoassay", SPIE vol. 1420 Optical Fibers in Medicine VI, pp. 2–9, 1991.
Stewart, G., et al., "Chemical sensing by evanescent field absorption: the sensitivity of optical waveguides", SPIE, vol.990 Chemical, Biochemical, and Environmental Applications of Fibers, pp. 188–195, 1988.
Heideman, Rene G., et al., "Simple interferometer for evanescent field refractive index sensing as a feasibility study for an immunosensor", Applied Optics, vol. 30, No. 12, pp. 1474–1479, Apr. 20, 1991.
Harrick, N. J., Internal Reflection Spectroscopy, pp. 27–43, 89–113, 1987.

Primary Examiner—Carol A. Spiegel

[57] ABSTRACT

A coupled pair of fiber optic fibers are used an immunoassay device. The fibers are first coupled and then drawn down to a single mode diameter. The coupler senses output ratio change due to chemical, biochemical, bioaffinity, immunogenic-type interactions and other molecular activity occuring within the evanescent field. The fusion joint of the coupler is coated with a first immunoassay component, and then surrounded with a second immunoassay component.

18 Claims, 8 Drawing Sheets

ANTIGENS ARE IMMOBILIZED ON THE SURFACE OF THE FO COUPLER

ANTIGENS SPECIFIC TO THE IMMOBILIZED ANTIBODIES BIND OR ATTACH

OTHER ANTIGENS NONSPECIFIC TO THE BOUND ANTIBODIES DO NOTHING

Y ANTIBODY SYMBOL
▼ ANTIGEN SYMBOL
Y̌ ATTACHMENT "LOCK & KEY"

■ ⎱ OTHER
● ⎰ ANTIGENS NON SPECIFIC

⋯ ⎱ FLUID MEDIUM BLOOD, URINE, AQUEOUS

FIBER OPTIC EVANSCENT WAVE SENSOR FOR IMMUNOASSAY

BACKGROUND OF THE INVENTION

1. Field of the Invention

This invention is in the field of immunoassay devices and methods where fiber optic sensors are used.

2. The Prior Art

Optical fiber consists of transparent material such as glass or plastic. Most optical fiber is fused silica and most plastic fiber is polymethylmethacrylate (PMMA). All optical fiber consists of a core and cladding of which the core has higher refractive index than the cladding. The fiber structure guides light by the process of total internal reflection (TIR). In silica fibers the core is usually established through doping with Germanium. PMMA uses a Fluorine polymer coating as the cladding. Fibers fall into two basic types, single mode or multimode. In single mode fibers the core is very small, 5 to 10 microns in diameter, for instance. Multimode fibers have cores of 50 to several thousand microns and very small cladding (in the order of tens of microns). Single mode fibers have a large cladding (usually more than 50 microns) making the fiber diameter generally 125 microns. The purpose of the large cladding in single mode fibers is to protect and contain the evanescent field of the single mode which extends into the cladding for several microns and can contain more than 10 percent of the optical energy normally thought of as traveling only through the core. Another importance of this larger diameter cladding is so that the fibers are hot too small for handling.

Fiber optic (FO) immunosensors for immunoassays may be classified as belonging to one of several categories. In the first type of fiber optic immunoassay sensor, a fiber is stripped of its cladding. To date these types of FO sensors have all been multi-mode. The various modes strike the glass air interface and are totally internally reflected. Just on the other side of the interface, where the reflection occurs, the light exists for a short distance in the physical form of an evanescent field. If a monoclonal or polyclonal antibody is attached to this surface, the field permeates this layer of antibody molecule but, there is little or no absorption or other phenomena which would otherwise change the amount of the light contained within the fiber. When antigens which have been labeled with fluorophores are attached, the evanescent field can cause the antigens to fluoresce causing an emittance which is optically detectable in a reduction in the light level or through collection of the fluorescence. In this way light energy is taken from the core through the evanescent field and is used to cause fluorescence. It is usually necessary to conjugate a fluorophore to the antigen to accomplish this application. If no antigen is bound, no fluorescent Output occurs. In some cases it is the unknown antigens which are attached and the antibodies are allowed to bind, assuming there is specificity to the fluorescent antibodies. The sensor can detect antigens or antigens and can be bound and the biosensor used to detect the presence of antibody (as in a disease state such as following infection with HIV or tuberculosis).

The fiber optic sensor can possibly replace many other immunodiagnostic modalities currently available. By binding the antigen, the sensor can probe unknown antibody. By binding an antibody, the assay can detect specific antigenic toxins or other immunogenic targets. Thus an organism is suspected to have been producing as a result of contact with an infectious agent.

The second type of fiber optic immunoasay sensor uses a coating deposited onto a fiber tip which may be illuminated with pulse which in turn induces fluorescence which is reflected back up the fiber and later detected. A beam splitter and possibly a filter is usually used to separate the pulses from the fluorescence. As in the first type, either antibody or antigen sensors may be constructed. Several options are available for tip and geometries. Review articles are available in Volume I and II of *Fiber Optic Chemical Sensors and Biosensors*, Otto S. Wolfbeis, ed., CRC Press, Boca Raton (1991). A specifically relevant article appears in Volume II, Vo-Dinh, et al., "Fiberoptics Immunosensors," Chapter 17, page 271–257.

A third type of fiber optic immunoassay sensor involves a stripped fiber which has antibodies or antigens attached to the core-air interface. This sensor, see R. G. Heideman, et al., "Simple interferometer for the evanescent field refractive index sensing as a feasibility study for an immunosensor," *Applied Optics*, Vol. 20, No. 12, pages 1474–1749 (1991), is used as one leg of a fiber optic Mach-Zehnder interferometer. The binding of molecules to the surface during attachment of either antibody or antigen suffices to locally change the index of refraction at the core solution interface. This occurs because the propagation constant of the cladding sets the speed of light within the core and some of this energy is in the cladding as an evanescent field, where the index is raised. Then, the phase velocity of the light changes and interference fringes are detected at the output of the interferometer.

Still other configurations of immunosensors have been described such as surface plasmon resonance immunosensors, and grating couplers used as integrated optical chemical sensors. These and others are discussed in the book edited by Wolfbels, op. cit..

The first type of fiber optic immunoasay sensors are fiber optic variations of internal reflection spectroscopy technology and are thoroughly described in *Internal Reflection Spectroscopy* by N. J. Harrick, Harrick Scientific Corporation, Ossining, N.Y. (1987). Harrick describes all kinds of geometries for these multimode sensors. A reference for the theory of fiber optics is *Optical Wave Guide Theory* by a W. Snyder and J. D. Love, Chapman and Hall, New York (1983). See also G. Stewart, et al., "Chemical sensing by evanescent field adsorption: the sensitivity of optical waveguides", "Proceedings of the international Society of Optical Engineering (SPIE)", Vol. 990, Boston,1988.

The evanescent field extends for only about one optical wavelength beyond the actual fusion joint surface. For light of 830 nm wavelength, it is not necessary to coat the fibers to more than one micron in thickness.

The advantages of coating single mode couplers are many. Conventional evanescent wave spectroscopy has been thoroughly described by N. J. Harrick, op. cit.. These are the techniques also used today in fiber optic sensing. The processes of detection usually rely on absorption processes in regions of a slab or waveguide where the evanescent field has penetrated the guide. In contrast, the single mode coupler sensor approach has evanescent field everywhere along the fusion joint. The guides are arranged so that as many reflections occur as possible. This is done by launching coherent light into the guide at angles which favor multiple reflections. Even so the numbers of places where ray optics allows interaction between the optical field and the chemical species are very few. The same thing happens in large core optical fibers; there is very little interaction area for the total area available. These sensors are only useful at the site where TIR takes place and so multiple reflections are used to amplify the effect. Even with favorable geometries the area of sensor surface which supports evanescent fields is small compared to the whole surface area.

Another problem with large core fibers is related to the relatively large number of spatial modes supported, possibly in the hundreds. The modes can and do interfere with each other leading on one hand to a finite number of modes and on the other hand to a speckle pattern occurring at the detector Snyder and Love, *Optical Waveguide Theory*, Chapman and Hall, N.Y. 1983. The detector can't distinguish the variations in light levels due to absorption from the many types of perturbations which cause speckle.

In contradistinction, single mode fibers only support the lowest order spatial mode and there is no speckle in these systems. Coupler sensors also are not subject to modal redistribution due to environmental effects. Another significant advantage of single mode fibers is that the evanescent field surrounds the entire space immediately surrounding the core. Couplers can locally force more than 90% of the optical energy into the evanescent field. It should be noted, however, that since single mode waveguides may not be analyzed using the ray optic approximation, electromagnetic waveguide theory must be applied.

SUMMARY OF THE INVENTION

This invention provides a sensitive detector having a wide variety of applications in the fields of biology, biochemistry and chemistry, and in many clinical applications as well. It uses a fiber optic coupler output ratio change due to the chemical/biochemical/bioaffinity/immunogenic-type interaction of bio-molecules (ligands) with their respective binding partners. The terms ligand and its binding partner for the ligand or, simply, binder will be used to represent the two components in specific bioaffinity binding pairs, all of which are capable of recognizing and binding with the other partner in a bimolecular recognition pair. Examples of such binding pairs include: antigen-antibody, substrate-enzyme, effector-enzyme, inhibitor-enzyme, complementary nucleic acid strands, binding protein-vitamin, binding protein-nucleic acid; reactive dye-protein, reactive dye-nucleic acid; and others. Either of the bindings partners is permanently attached to the fusion joint of a single mode coupler and within the evanescent field for very specific and direct detection of minute concentrations of an analyte of interest (one of the components of the binding pair) within the tested sample without the need to label a reagent. The biomolecule may be linked to the surface of the fusion joint by means of a spacer molecule.

In the following the invention will occasionally be specifically described with reference to immunosensors, it being understood that the invention is in no way confined thereto and covers quite generally chemical sensors within the meaning of this term as defined hereinabove. In particular, beyond immunosensors, this invention has an application to an additional field of chemistry which is binding of nucleotides, cDNAs, riboprobes, genetic DNA or RNA molecules using the principles of solution hybridization. This expands the scope of the immunosensor to a "nucleotide sensor" with potential for wide applications in many aspects of the field of molecular biology. The binding of single stranded synthetic oligonucleotides (or cDNA or genomic DNAs) to the fiber optic will allow for the detection of the complimentary DNA strand or RNA. This application has potential uses in many areas: 1) the evaluation of levels of mRNA expression in tissues, e.g., the determination of tissue specificity of gene expression; 2) the detection of viral or other rare DNAs; 3) forensic science, paternity testing. The sensor may also substitute for Northern or Southern or Dot blots in some instances.

Construction of conventional single mode evanescent wave spectrometer systems involves stripping or exposing the fiber core by removal of the fiber's protective cladding. As in conventional evanescent wave spectroscopy, there is an absorption of light at some particular wavelength and, as a result, the detector experiences a lowering of the optical intensity level as light is extracted at the exposed core section of the fiber. It should be appreciated that optical power levels are extremely difficult to measure in absolute terms; the best photometers commonly available are only accurate to about 1%. Relative measurements may be measured with much more accuracy but longer term measurements are subject to drift. Signal drift occurs at the detector, in the transimpedance amplifiers behind the detector, at the laser source and it's driving electronics, and even in the fiber and connectors. Signal drift is difficult to separate from sensor activity without some kind of a reference.

Coupler sensors with a single mode, share the advantages of the conventional single mode sensors. However, absorption is not necessary and is not even desirable for the operation of the sensor. As the coupler output ratio is extremely sensitive to the refractive index of the medium which surrounds the fusion joint of the coupler, chemical changes occurring near the fusion joint will cause a trading of power between the output channels. Changes in refractive index of one part in a million have been measured with the simple hand-held optical power meters used in fiber optics communication systems.

Coupler sensors provide a signal processing advantage which is important to the measurement of small signal changes. Since there is no signal lost to absorption, the two coupler output channels will sum to a constant level even though the coupling ratio may change drastically. The dual output provides a total separation of drift variables from sensor variables. Difference over sum signal processing is also available as are a number of attractive electronic methods common to self referenced systems. Thus in view of this consideration in the construction of antibody conjugated optical fiber couplers may provide useful probes for detecting soluble ligands and similarly, the construction of nucleotide sensors, with conjugate DNA or RNA, may provide improved methods for detection of complimentary DNA or RNA.

The development of coupler fabrication technologies now provide an electric furnace method of biconical coupler fabrication. A coupler fusion electric furnace taught by U.S. Pat. No. 4,879,454, Gerdt, (incorporated herein by reference) allows inexpensive production of single mode couplers.

The remarkable sensitivity of coupler sensors has been documented, see D. W. Gerdt, L. H. Gilligan, "Variable Coupler Fiber Optic Sensor", *Proceedings of the international Society of Optical Engineering* (SPIE), Vol. 835, 1987, D. W. Gerdt, "Applications of Fiber Optic Coupler Sensors,"*Proceedings of the International Society of Optical Engineering* (SPIE), Vol. 990 Boston, 1988, and D Gerdt, "Fiber Optic Coupler Sensors," *Naval Eng. Journal*, May 1990, 275–280). Coupler sensors can be used in an assay method for very dilute, specific antigens, e.g., proteins including glycoproteins. The attachment of polyclonal antibodies can be used as screening tests for one or more of several specific antigens. The coupler output ratio depends very strongly on the refractive Small changes in index change greatly or even switch totally the division of optical power between the output fibers.

An antibody which is immobilized on the surface of the fusion joint can be used as an assay for a specific antigen. The basic concept of the fiber optic coupler also applies to DNA/RNA chemistries as well, provided conjugation methods to the couplers are developed. A coupler-antibody system can be prepared with an antibody and then exposed to a test solution containing an antigen capable of binding with this antibody. Upon first contact the coupler output ratio will immediately change to a certain value. This value will remain constant if no specific antigens are present. As the reaction proceeds, the antigen capable of binding with the antibody, if present, will begin to bind to the antibody until the degree of binding reaches an equilibrium value after a few minutes. The binding will occur only within the evanescent field of the coupler where the output ratio of the coupler is determined. Binding changes dramatically the electronic distribution of the original fusion joint coating because the index of refraction depends almost entirely on electronic arrangement and densities.

The rate at which the coupling ratio changes depends on the concentration of the analyte in solution. A coupler sensor used in this manner acts as an antibody immobilized on a solid support in an immunoassay.

DETAILED DESCRIPTION OF THE INVENTION

Figure 1:
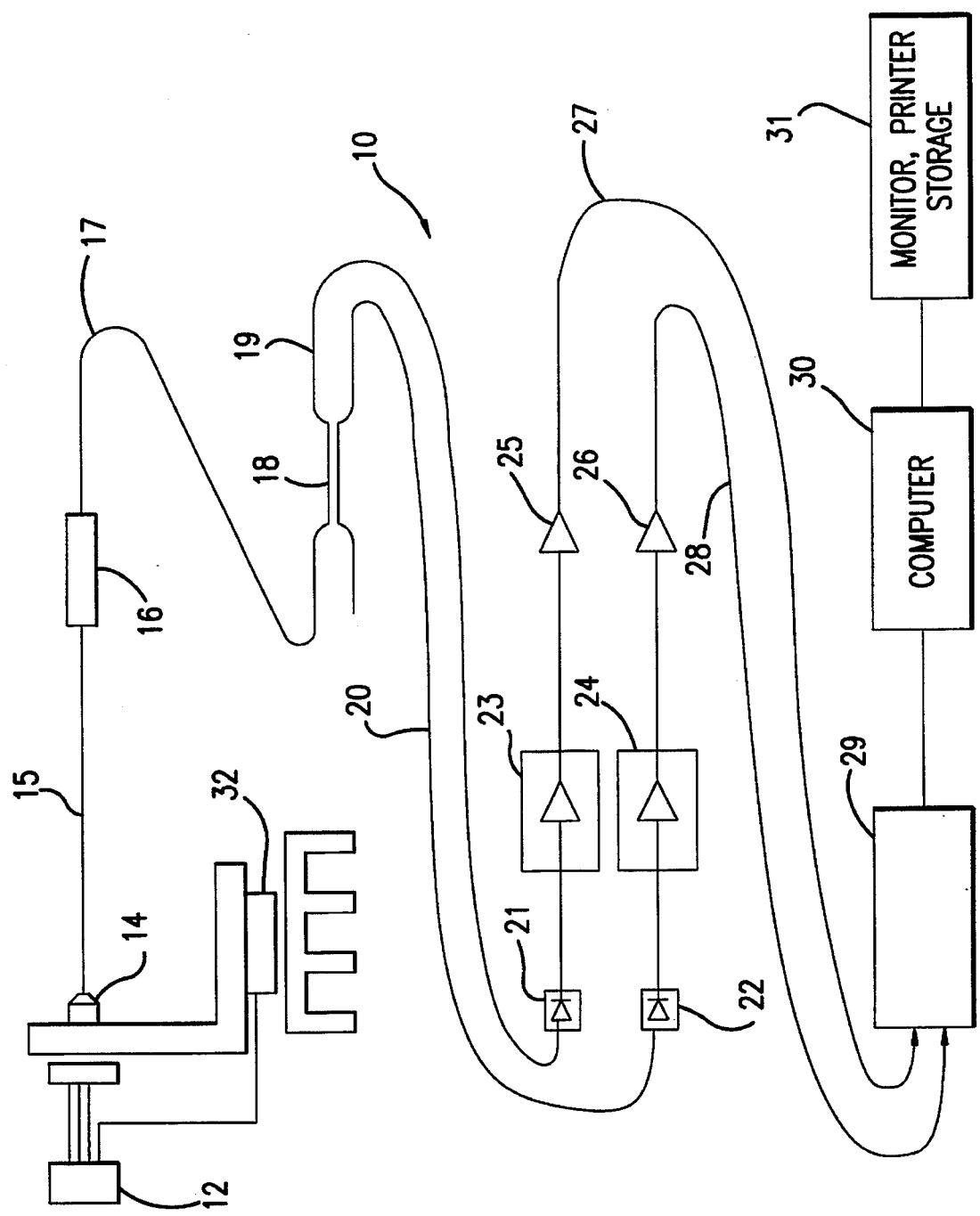
FIG. 1 is a flow diagram of an immunoassay system based upon a fiber optic coupler in accordance with this invention.

In FIG. 1, there is shown an overall fiber optic system diagram 10 in accordance with this invention. A laser driver 12 is connected to a laser diode 14, which is in turn, connected to a pig tail fiber 15 which passes light from the laser to a fiber optic splice 16. Light exits the splice 16 and is inserted into a first leg 17 of a fiber optic coupler 18. Light entering the first leg 17 of the coupler 18 exits on the same fiber at a fiber optic conductor 19 (input channel). A second fiber optic output 20 (output channel) provides an output for light from the first leg 17 which is coupled and inserted into a fiber 20. A first photo diode detector 21 is connected to the fiber optic conductor 19 and a second photo diode detector 22 is connected to the fiber 20. The first photodiode detector 21 has its output connected to a first transimpedance amplifier 23; the second photodiode detector 22 has its output connected to a second transimpedance amplifier 24. The outputs of the transimpedance amplifiers 23, 24 are applied to A/D converters 25 and 26 which provide digital electrical signals along wires 27 and 28 to an instrumentation board 29. The instrumentation board 29 is then connected to a personal computer 30 which provides outputs for a monitoring devices 31, preferably a printer or a monitor. A peltier cooler 32 is used for stabilizing the wavelength of the laser driver 12.

The laser diode 14 may be a pigtailed Sharp LT 023 MS laser diode having a fiber such as a Corning FLEXCOR 850. Both lasers and incoherent sources such as light emitting diodes may be used. The laser driver 12 may be a MELLES GRIOT 06 DLD 103 diode laser driver which stabilizes the output of the pigtailed laser diode 14 so as to achieve stability in terms of both milliwatts of optical power and the optical wavelength.

The first and second diode detectors 21 and 22 may be silicon diode detectors, gallium arsenide (GaAs) detectors. Other detectors which may work better at different wavelengths are also contemplated within the scope of this invention. 800 µm sensitive photo diodes have been used, and 1300 µm sensitive photodiodes may be used.

The transimpedance amplifiers 23 and 24 are preferably MELLES GRIOT 13 AMP 003 large dynamic range amplifiers. Preferably, a single transimpedance amplifier is used for each output channel.

The A/D converters 25 and 26 are preferably HP 3578A multimeters manufactured by Hewlett-Packard Co.

Figure 2:
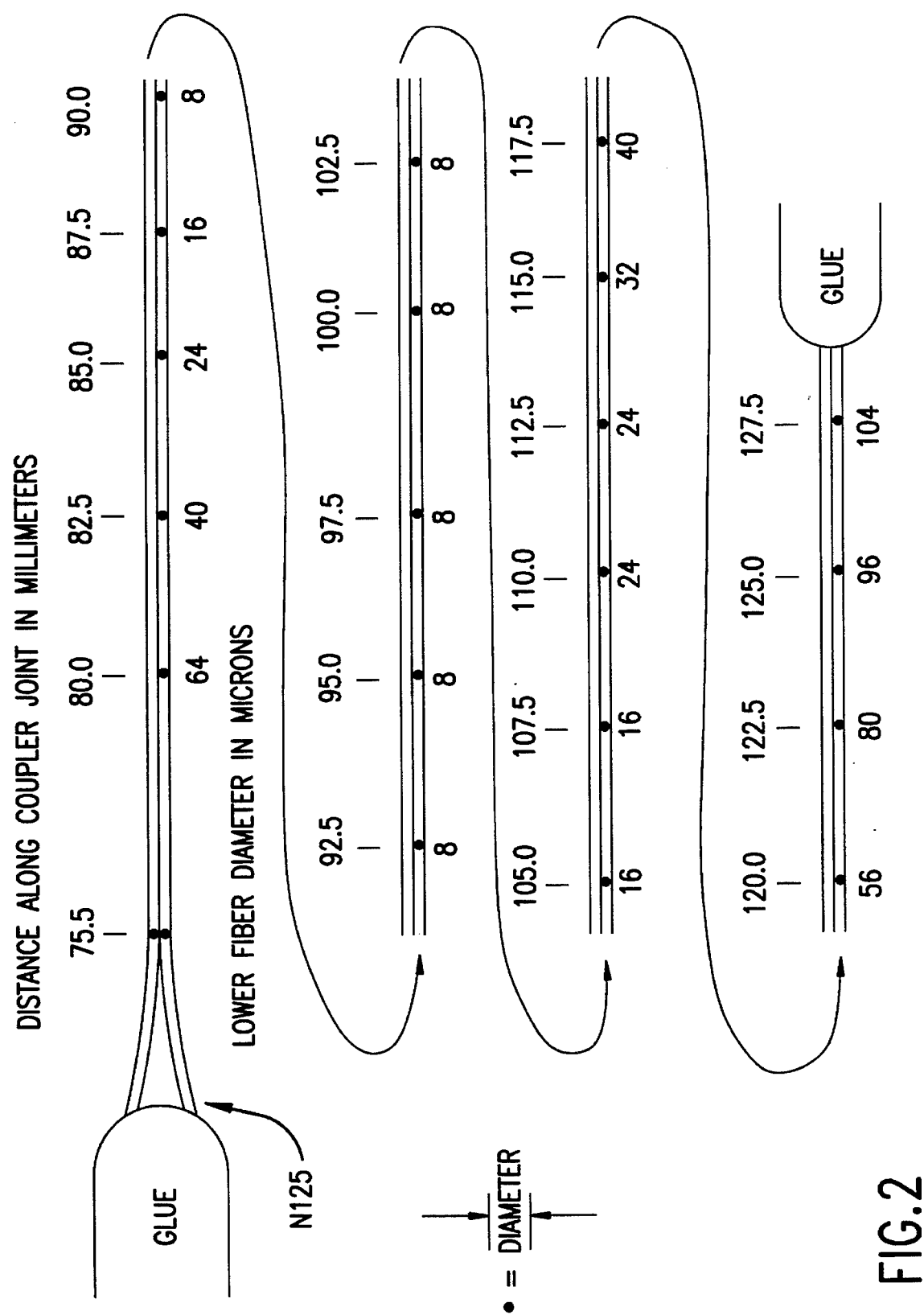
FIG. 2 shows a coupler joint, or a drawn fiber pair.

FIG. 2 shows a typical size for a single mode fiber optic coupler. Here, there is shown a fused drawn fiber optic coupler. The diameter of the fused section reduces from about 125 microns to about 8 microns (the waist region) and then increases again back to the fiber diameter such as 125 microns. Because of the small size of the coupling the evanescent field of the fiber optic conductors is pushed outward into the medium surrounding the coupling.

Figure 3:
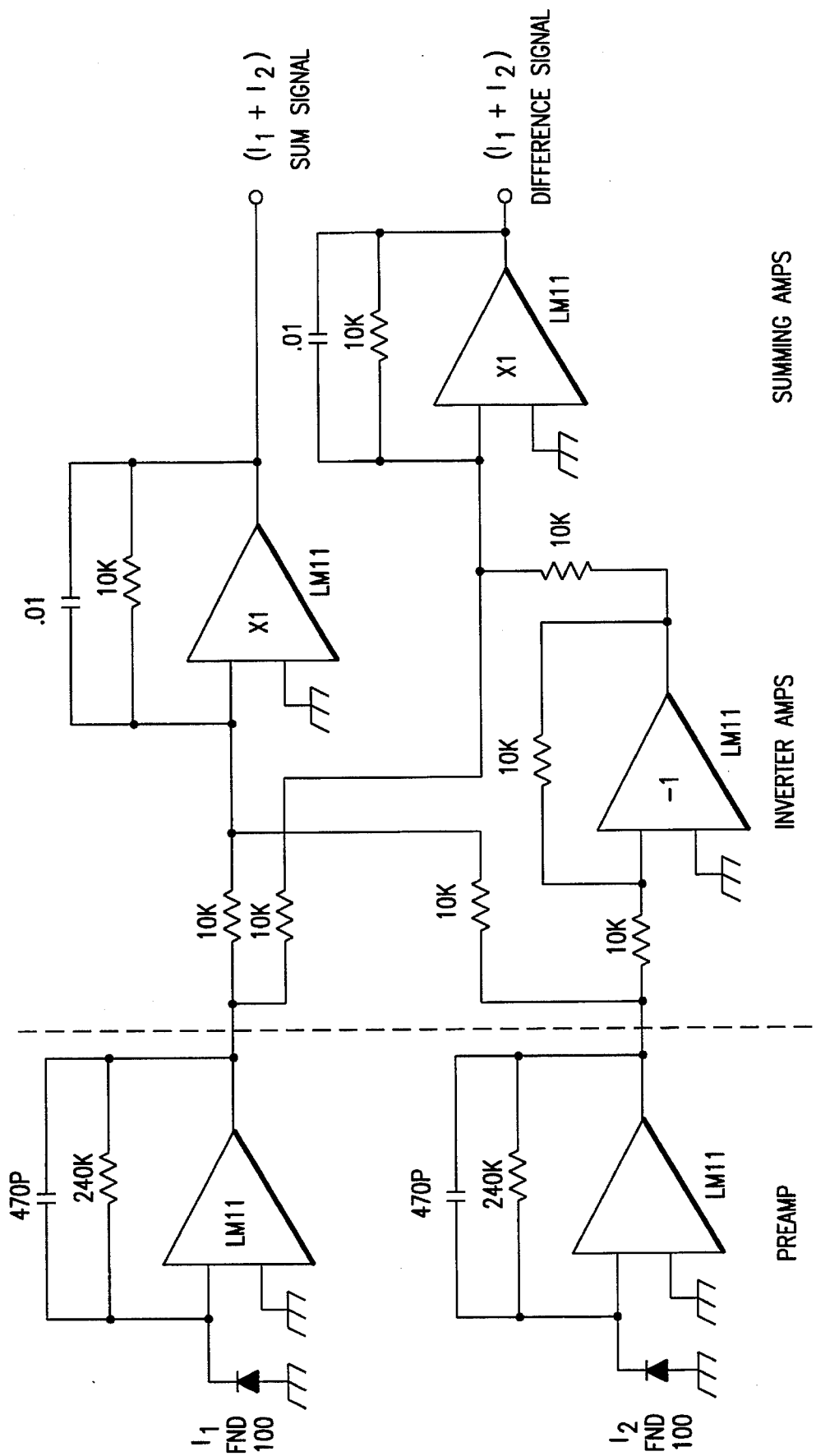
FIG. 3 shows a detailed diagram of the transimpedance amplifier and photo diodes used for producing the sum and difference signals referred to in FIG. 1.

FIG. 3 depicts a typical arrangement of a transimpedance amplifier system with an instrumentation amplifier system in accordance with this invention. The amplifiers LNII (National Semiconductor Corp.) in the preamplification stage convert a current output from the fiber optic couplers to a voltage output at the input to the inverter amplifiers. Sum and difference signals are produced in the conventional manner.

Figure 4:
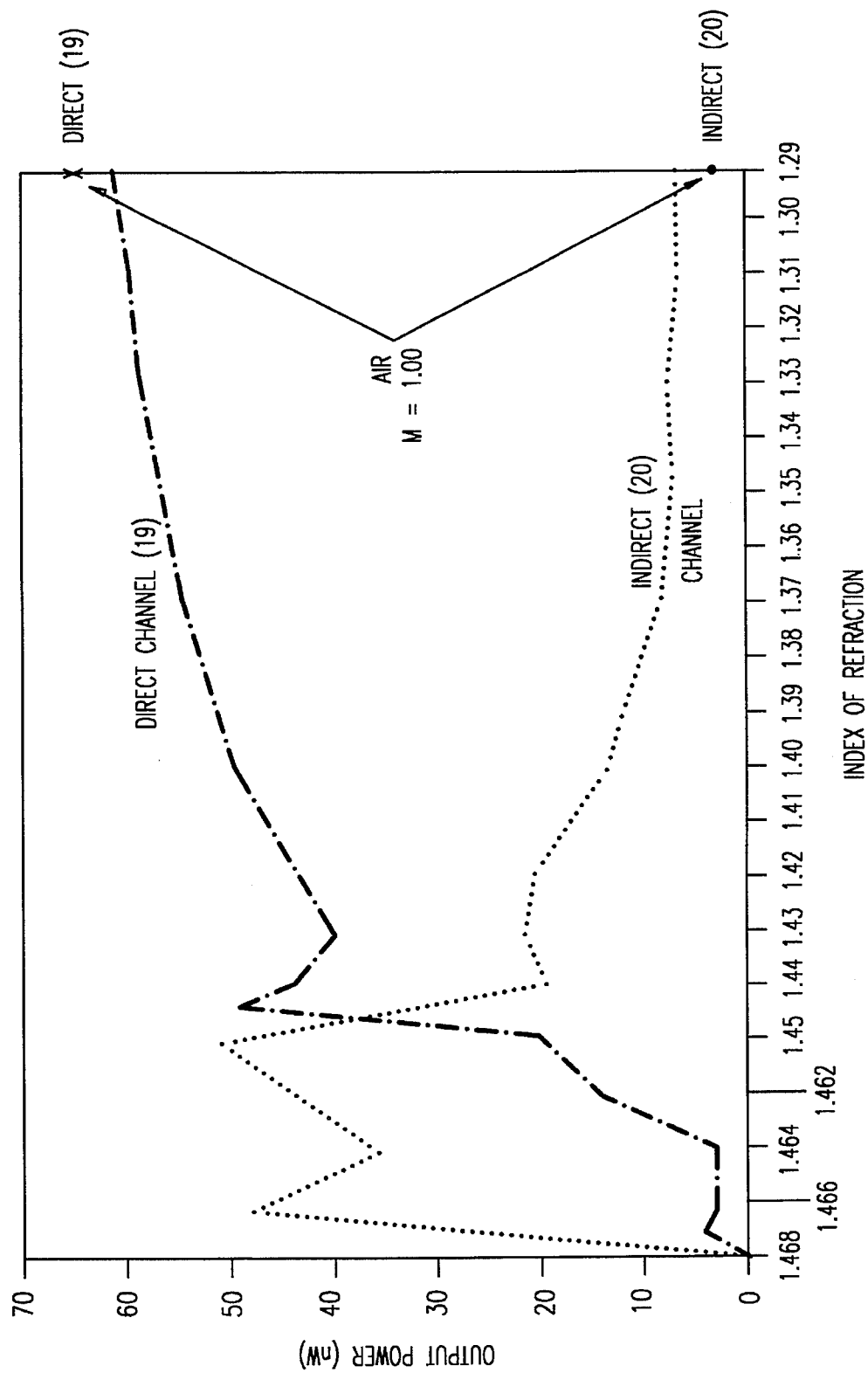
FIG. 4 shows a sensitivity of an underdrawn coupler to the refractive index.
Figure 5:
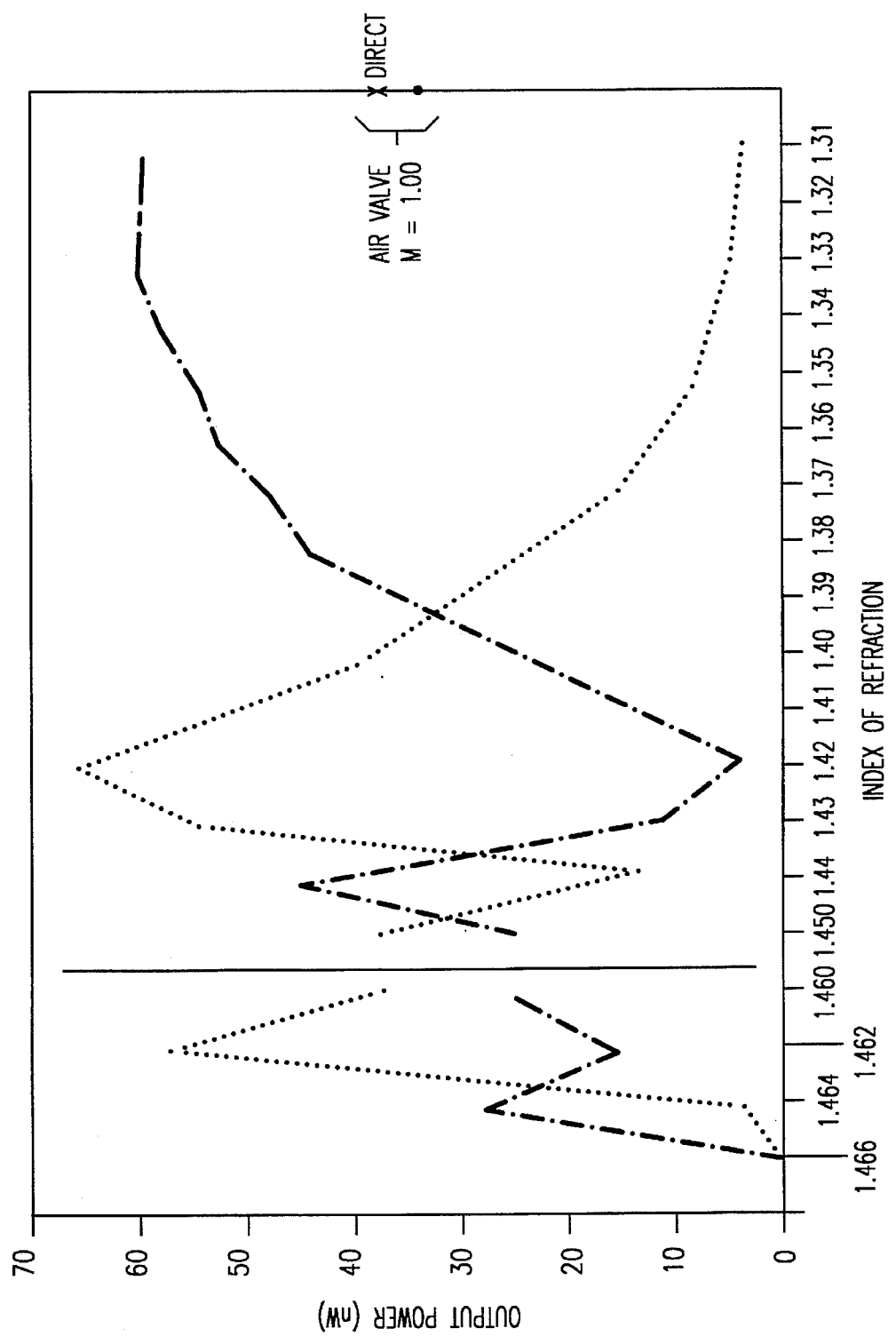
FIG. 5 shows the sensitive of a balanced (in air) coupler to refractive index.
Figure 6:
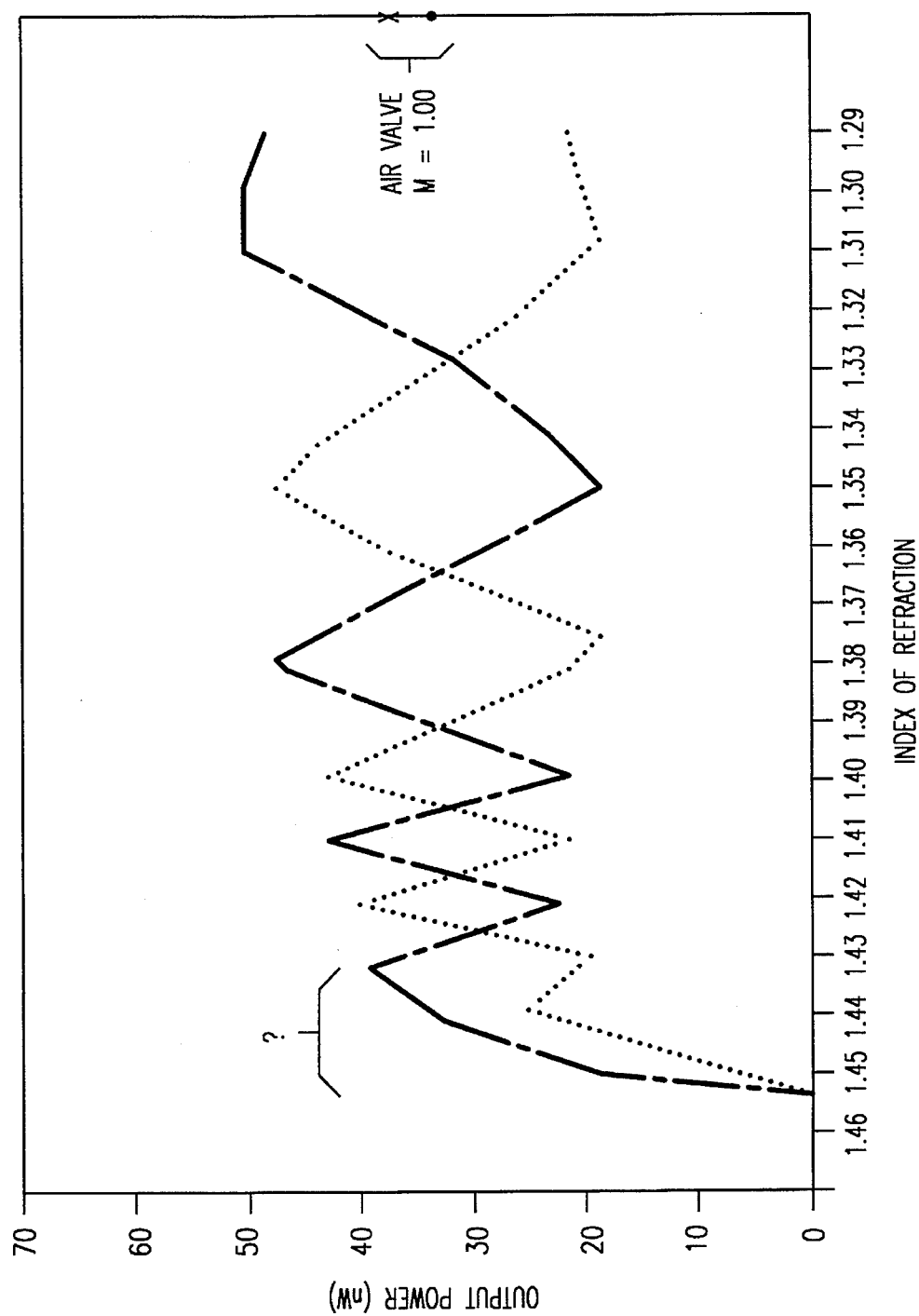
FIG. 6 shows a sensitivity of an overdrawn coupler to refractive index.

FIGS. 4, 5 and 6 show diagrams of the sensitivity of a coupler which has been underdrawn, balanced, and overdrawn. Referring now to FIG. 4, the underdrawn coupler is shown to have a substantial output power difference between the output of the direct coupler 19 (FIG. 1) and the output of the indirect coupler 20 in air. As the index of refraction increases, the output power of the direct channel 19 decreases and the output power of the indirect channel 20 increases. Higher sensitivity is achieved where the coupler is drawn beyond the balance point and into an overdrawn state. This can be seen in FIG. 6 where the power of the direct and indirect channels changes rapidly which can be seen as a substantial slope in each segment of the curves. In this condition, very little change in index of refraction will result in a large difference in light magnitude between the direct and indirect channels, as well as a substantial difference in each channel. In the balanced coupler state, as shown in FIG. 5, the coupler is more sensitive than in the underdrawn (FIG. 4) and has a fairly linear large dynamic range (output power from 5nw to 65nw. It should also be observed that in the overdrawn case, the linear dynamic range is decreased, although the sensitivity is increased.

In this invention, when the coupler is drawn to its single mode condition, the evanescent field surrounding the coupling is forced outside of the glass perimeter. The presence or absence of material which affects the index of refraction of the molecules in the evanescent field is detected by observing the magnitude of the light passing through each channel and the difference between the light in each channel. An apparatus for constructing a coupler of the type used in this invention is shown in U.S. Pat. 4,879,454, Gerdt, which is incorporated herein by reference.

Figure 7:
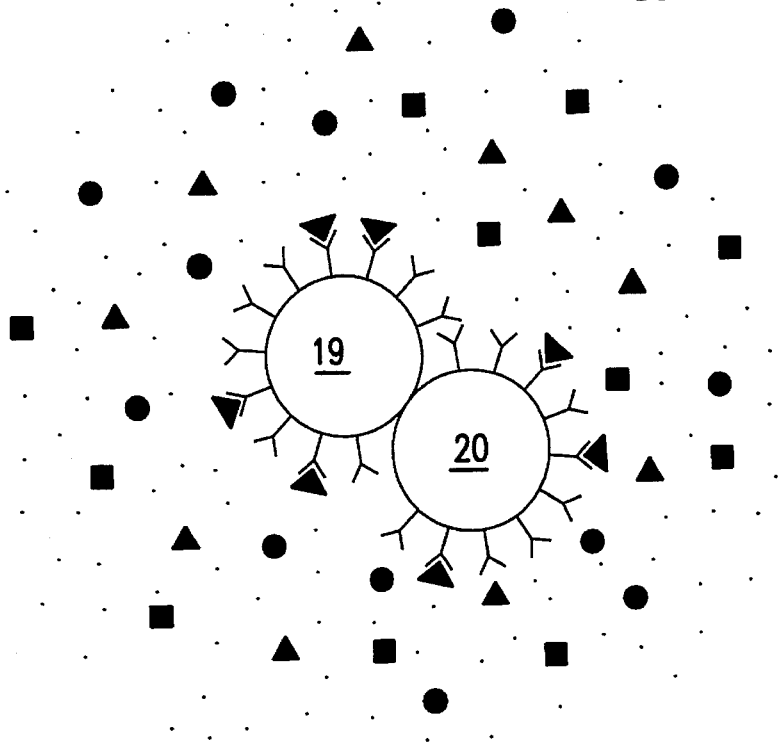
FIG. 7 shows a representational sketch of a fiber optical coupler which has been prepared with antibodies attached and inserted into a solution containing antigens to form a coupler antibody system.

In FIG. 7, there is shown, in representational form, a pair of coupled fiber optic conductors 19 and 20. The area immediately surrounding the coupling is shown as having attached to the conductors antibodies or analogue antibodies which have "Y" symbol. Antigens or analogue antigens which are specific to antibodies "Y" are generally shown as a darkened triangle. Other antigens which are non specific to the antibody "Y" are shown as squares and solid circles. When the attachment or combination of a "Y" and a shaded triangle is made, there is a change in the index of refraction as a result of this new molecule residing in the evanescent field surrounding the coupled conductors. Although the bimolecular recognition pair depicted in FIG. 7 is assumed herein to be an antibody-antigen for use in immunoassays, it should be understood that the invention is in no way confined thereto and covers quite generally chemical sensors within the meaning of this term as defined hereinabove; the drawings are provided to conceptually illustrate of the functioning of the inventive fiber optic sensor in immunoasays, but in no way to limit the present invention.

Figure 8:
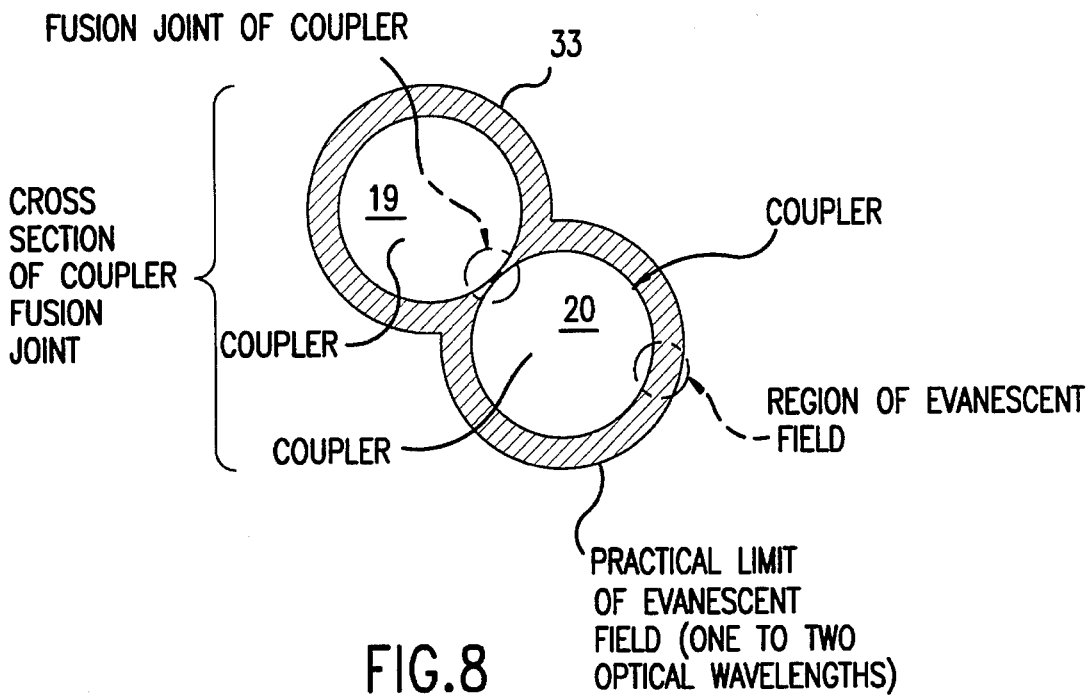
FIG. 8 shows a representational sketch of the joint of a coupler including the region of the evanescent field.

In FIG. 8, there is shown a representation of the coupling of light conductors 19 and 20 with the evanescent field surrounding the coupler surface. At the practical limit, the evanescent field extends one or two optical wavelengths outward from the coupler surface. The field is generally indicated at reference numeral 33.

Figure 9:
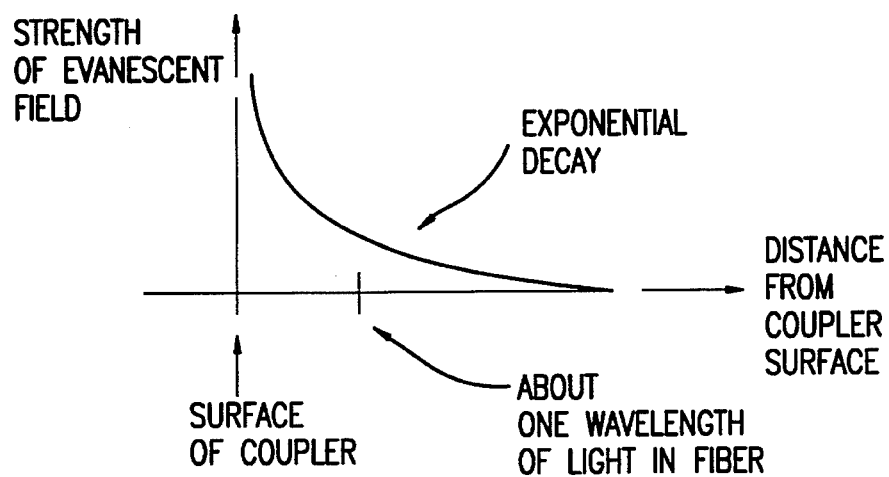
FIG. 9 shows a graph depicting the relationship of the strength of and evanescent field to distance from a coupler surface.

In FIG. 9, there is shown a representation of the exponential decay of the evanescent field as distance from the coupler surface increases. At approximately one wavelength, the exponential decay becomes substantial, and the strength of the field is decreased to the point where it is not very useful in that it is difficult to use the outer or weaker portion of the field to detect changes in index of refraction resulting from changes in molecular structure in this region.

What is claimed is:

1. A fiber optic sensor for immunoassay comprising:

a fiber optic coupler having a plurality of input optical fibers each having a core;

said cores being coupled for exchange of optical signals in a waist region;

a plurality of output optical fibers emerging from said waist region;

said fiber optic coupler distributing an input optical signal incident to one of said input optical fibers between said plurality of output optical fibers;

a first immunoreactant coated on said waist region, wherein said first immunoreactant is capable of specifically binding to a target analyte and wherein said first immunoreactant is an antibody or an antigen;

means for inserting light into at least one of said input optical fibers, whereby an evanescent region is produced surrounding said waist region;

means for measuring light magnitude emitted from a plurality of said output optical fibers; and means for comparing the magnitude of light emitted at least two of said output optical fibers.

2. The fiber optic sensor in accordance with claim 1 wherein the first immunoreactant is an antibody and is coated on said waist region and wherein the target analyte is an antigen.

3. The fiber optic sensor in accordance with claim 1 wherein the first immunoreactant is an antigen and is coated on said waist region and wherein the target analyte is an antibody.

4. The fiber optic sensor in accordance with claim 1 wherein the evanescent filed extends approximately 1 wavelength beyond said waist region.

5. The fiber optic sensor in accordance with claim 1 wherein the fiber optic coupler is a single mode coupler.

6. The fiber optic sensor in accordance with claim 1 wherein said light inserted into said at least one input optical fiber is coherent light.

7. The fiber optic sensor in accordance with claim 1 wherein said means for measuring the magnitude of light comprises a light meter.

8. An immunoassay sensor comprising in combination:

a fiber optic coupler having a fusion joint;

means for light input into said fiber optic coupler, whereby an evanescent field is produced surrounding said fusion joint;

a first immunoassay reagent attached to the fusion joint and within said evanescent field, whereby said first immunoassay reagent is capable of specifically binding to a target immunoreactant;

means for detecting a light output ratio change due the specific binding of the target immunoreactant to said first immunoassay reagent.

9. The immunoassay sensor in accordance with claim 8 wherein said fusion joint is of a single mode coupler.

10. The immunoassay sensor according to claim 8 wherein said first immunoassay component is an antigen.

11. The immunoassay sensor according to claim 8 wherein said first immunoassay component is an antibody.

12. A method of immunoassay measurement of a target component comprising the steps of:

forming a coupler fusion joint from a plurality of single mode fiber optic fibers;

coating the fusion joint of the coupler with a first immunoassay component capable of specifically binding to the target component;

surrounding the coated fusion joint of the single mode fiber optic coupler with the target component;

inserting light into one of said optic fibers after coating the fusion joint;

measuring light output from two or more the optic fibers before and after surrounding the fusion joint with the target component; and determining the presence or concentration of the target component by measuring changes in the output of light from said two or more optic fibers due to the specific binding of the target component to the first immunoassay component.

13. A biosensor for detecting a target nucleic acid sequence comprising:

a single mode optical fiber coupler having coated thereon a first oligonucleotide capable of hybridizing to said target nucleic acid sequence;

a means for inputting light into the single mode optical fiber coupler, whereby an evanescent region is produced around the single mode optical fiber coupler; and a means for detecting a light output ratio change due to hybridizing of the target nucleic acid sequence to said first oligonucleotide.

14. A biosensor in accordance with claim 13, wherein said first oligonucleotide is selected from the group consisting of sense cDNA, anti-sense cDNA and genomic DNA and RNA.

15. A method of immunoassay or nucleic acid hybridization measurement of a target component in a fluid comprising the steps of:

making a single mode fiber optic coupler comprising a fusion joint of at least two single mode optical fibers;

making a biosensor by coating the fusion joint of the coupler with a first measurement material capable of specifically binding to or hybridizing to the target component wherein the first measurement material is selected from the group consisting of an antigen, an antibody and a nucleic acid sequence;

surrounding the fusion joint of the coupler with the target component wherein the target component is selected from the group consisting of an antigen, an antibody and a nucleic acid sequence capable of being specifically bound or hybridized to the biosensor;

inserting light into one of said optical fibers;

measuring and summing the output of light from two of more of the optical fibers before and after surrounding the coupler with the target component; and determining the presence or concentration of the target component in the fluid by comparing changes in the light output levels of said two or more optical fibers due to the specific binding or hybridization of the target component to the first measurement material.

16. The method of measurement in accordance with claim 15 wherein said first measurement material is selected from the group consisting of an oligonucleotide, cDNA, RNA, and genomic DNA.

17. The method of measurement in accordance with claim 15 wherein said step of measuring and summing comprises a plurality of measurements made over a predetermine time interval and further determining rate of change of the light output and said step of comparing comprises comparing the rate of change of the light output as an indication of the concentration of the target material in the fluid.

18. An immunoassay method for determining a target analyte in a fluid sample, which method does not use labeled reagents and is based upon measuring changes in refractive index in an evanescent field surrounding a fiber optic coupler, comprising:

providing a fiber optic coupler comprised of a plurality of optical fibers which are first coupled and then drawn to a single mode diameter;

immobilizing an antibody or antigen capable of specifically binding to the target analyte on the fiber optic coupler;

illuminating at least one of the plurality of optical fibers to provide the surrounding evanescent field;

obtaining a first refractive index of the surrounding evanescent field by measuring a first ratio of light output by the fiber optic coupler;

contacting the fluid sample to the fiber optic coupler such that any target analyte in the fluid sample specifically binds to the immobilized antibody or antigen;

obtaining a second refractive index of the surrounding field by measuring a second ratio of light output by the fiber optic coupler; and determining the presence or concentration of the target analyte in the fluid sample by measuring the change in refractive index produced by specific binding of the target analyte to the immobilized antibody or antigen on the fiber optic coupler.

* * * * *